United States Patent [19]

Kitazawa et al.

[11] Patent Number: 5,177,069
[45] Date of Patent: Jan. 5, 1993

[54] NAPHTHYSULFONYLALKANOIC ACID COMPOUNDS AND PHARMACEUTICAL COMPOSITIONS THEREOF

[75] Inventors: Makio Kitazawa; Masuo Akahane, both of Matsumoto; Yasushi Nakano, Shiojiri; Atsushi Tsubaki, Matsumoto; Kazuaki Sato, Matsumoto; Masaaki Ban, Matsumoto; Michihiro Kobayashi, Akashina, all of Japan

[73] Assignee: Kissei Pharmaceutical Co., Ltd., Japan

[21] Appl. No.: 623,107

[22] Filed: Dec. 6, 1990

[30] Foreign Application Priority Data

Dec. 13, 1989 [JP] Japan .................. 64-323508
Dec. 16, 1989 [JP] Japan .................. 64-337849
Dec. 22, 1989 [JP] Japan .................. 64-334543

[51] Int. Cl.⁵ ............... A61K 31/395; A61K 31/195; A61K 31/24; A61K 31/40; C07D 265/30; C07D 211/06; C07D 207/04; C07C 321/06
[52] U.S. Cl. .................. 514/210; 514/211; 514/212; 514/237.8; 514/331; 514/428; 514/510; 514/562; 544/159; 546/206; 548/531; 548/542; 548/550; 548/568; 548/572; 560/10; 562/427

[58] Field of Search ............ 560/10; 562/427; 514/510, 210, 211, 212, 237.8, 331, 428, 562; 544/159; 546/206; 548/531, 542, 550, 568, 572

[56] References Cited

U.S. PATENT DOCUMENTS 4,447,452  5/1984  Sestanj .................. 562/427 X
4,752,616  6/1988  Hall et al. .............. 514/510

Primary Examiner—José G. Dees
Assistant Examiner—Vera C. Clarke
Attorney, Agent, or Firm—Depaoli & O'Brien

[57] ABSTRACT

The present invention provides a novel class of naphthylsulfonylalkanoic acid compounds such as a structure corrresponding to the formula:

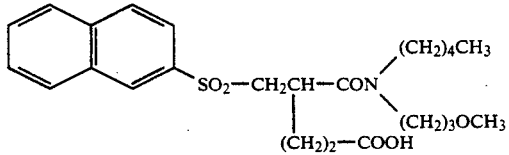

or a pharmaceutically acceptable salt thereof.

A present invention naphthylsulfonylalkanoic acid compound is useful for prevention or treatment of irritable bowel syndrome, biliary dyskinesia and acute pancreatitis.

7 Claims, No Drawings

NAPHTHYSULFONYLALKANOIC ACID COMPOUNDS AND PHARMACEUTICAL COMPOSITIONS THEREOF

FIELD OF THE INVENTION

The present invention relates to naphthylsulfonylalkanoic acid compounds being useful for therapeutic agents.

More particularly, the present invention relates to novel naphthylsulfonylalkanoic acid compounds represented by the formula:

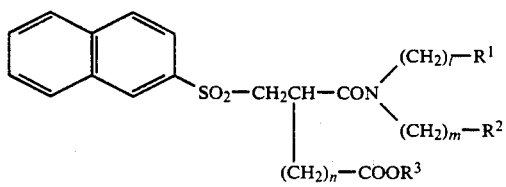

wherein $R^1$ represents a hydrogen atom, an alkyl group having 1 to 6 carbon atoms, a cycloalkyl group having 3 to 6 carbon atoms, an alkoxy group having 1 to 6 carbon atoms, an alkenyloxy group having 3 to 6 carbon atoms, an acyloxy group having 2 to 5 carbon atoms, a carboxy group, an alkoxycarbonyl group having 2 to 7 carbon atoms, a carbamoyl group of the formula

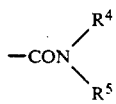

in which $R^4$ and $R^5$ are the same or different and are a hydrogen atom or an alkyl group having 1 to 6 carbon atoms, a group of the formula

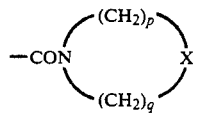

in which X is a single bond, —$CH_2$— or —O—, p and q are the same or different and are an integer of from 0 to 3, with the proviso that the sum of p and q is 2 to 5, or a lactam group of the formula

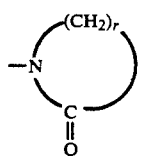

in which r is an integer of from 2 to 5; $R^2$ represents a hydrogen atom, an alkyl group having 1 to 6 carbon atoms, a cycloalkyl group having 3 to 6 carbon atoms, an alkoxy group having 1 to 6 carbon atoms, an alkenyloxy group having 3 to 6 carbon atoms, an acyloxy group having 2 to 5 carbon atoms or an alkoxycarbonyl group having 2 to 7 carbon atoms; $R^3$ represents a hydrogen atom, an alkyl group having 1 to 4 carbon atoms or a benzyl group; l and m are the same or different and are an integer of from 1 to 4; n is 1 or 2; and pharmaceutically acceptable salts thereof.

BACKGROUND OF THE INVENTION

Cholecystokinin, hereinafter referred to as CCK, is a typical gastrointestinal hormone with activity that stimulates exocrine pancreatic secretion and contracts the gallbladder.

PRIOR ART

Analogs of Proglumide represented by the formula:

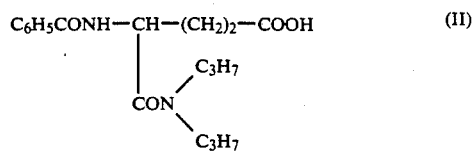

are reported in patent applications which include Japanese Patent Application (OPI) Nos. 44855/86, 181246/87, 27468/88, 165352/88 and 201156/88 (The term "OPI" used herein refers to an unexamined Japanese Patent Application), EP(A1)0308885, EP-(A2)0272228, WO87/03869, WO88/05774 and WO89/02431. The compounds described in these patent applications are derived from amino acid compounds such as glutamic acid or aspartic acid.

The present invention provides novel naphthylsulfonylalkanoic acid compounds which exhibit strong antagonistic activities toward CCK receptors, and thus they are useful as therapeutic agents for the prevention and treatment of irritable bowel syndrome, biliary dyskinesia and acute pancreatitis.

SUMMARY OF THE INVENTION

An object of the present invention is to provide novel naphthylsulfonylalkanoic acid compounds which exhibit a strong antagonistic activity toward CCK receptors.

A further object of the present invention is to provide pharmaceutical compositions containing a naphthylsulfonylalkanoic acid compound as an active ingredient.

Other objects, features and advantages of the present invention will be apparent from the following description of the invention.

DETAILED DESCRIPTION OF THE INVENTION

The present invention provides naphthylsulfonylalkanoic acid compounds which exhibit antagonistic activity toward CCK receptors.

The naphthylsulfonylalkanoic acid compounds of the present invention competitively inhibit CCK-8 from binding to CCK receptors, and thus exhibit inhibitory activities against gallbladder contraction and amylase secretion by CCK-8.

Thus, the naphthylsulfonylalkanoic acid compounds of the present invention are useful as therapeutic agents for the prevention or treatment of irritable bowel syndrome, biliary dyskinesia and acute pancreatitis.

The term "alkyl" in the present invention refers to a straight or branched alkyl group having 1 to 6 carbon atoms, such as methyl or isobutyl.

The term "alkoxy" in the present invention refers to a straight or branched alkoxy group having 1 to 6 carbon atoms, such as methoxy or isopropoxy.

The term "alkenyloxy" in the present invention refers to a straight or branched alkenyloxy group having 3 to 6 carbon atoms, such as allyloxy or 2-butenyloxy.

The term "acyloxy" in the present invention refers to a straight or branched acyloxy group having 2 to 5 carbon atoms, such as acetoxy, propionyloxy, butyryloxy, isobutyryloxy, valeryloxy, isovaleryloxy, 2-methylbutyryloxy and pivaloyloxy.

The term "cycloalkyl" in the present invention refers to a cycloalkyl group having 3 to 6 carbon atoms, such as cyclopropyl, cyclobutyl, cyclopentyl and cyclohexyl.

The substituent

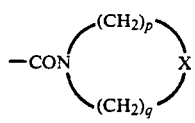

in the present invention formulas refers to structures such as 1-pyrrolidinylcarbonyl, piperidinocarbonyl, morpholinocarbonyl, and the like.

The term "lactam" in the present invention refers to structures such as 2-oxo-1-pyrrolidinyl, 2-oxopiperidino, and the like.

The novel naphthylsulfonylalkanoic acid compounds of formula (I) can be prepared by oxidizing naphthylthioalkanoic acid compounds represented by the formula:

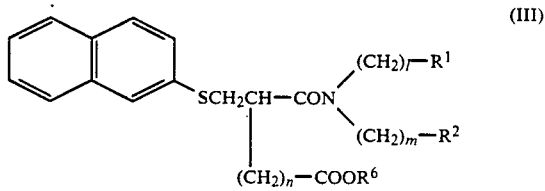

wherein $R^1$, $R^2$, l, m and n are as previously defined; and $R^6$ represents an alkyl group having 1 to 4 carbon atoms, or a benzyl group. The corresponding carboxylic acid compounds can be prepared by hydrolysis or hydrogenolysis of the ester products.

The compounds of formula (I), wherein $R^1$ is a carboxy group, a substituted or unsubstituted carbamoyl group or a group of the formula

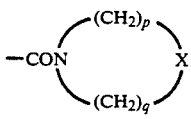

in which p, q and X are as previously defined, also can be prepared by hydrolyzing compounds of formula (I), when $R^1$ is tert-butoxycarbonyl group, with trifluoroacetic acid to remove said protective group, or as appropriate by amidating the product.

The formula (I) compounds wherein at least one of $R^1$ and $R^2$ is an alkoxycarbonyl group or an acyloxy group, and $R^3$ is a hydrogen group also can be prepared by hydrogenolysis of formula (I) compounds in which $R^3$ is a benzyl group. The formula (I) compounds wherein at least one of $R^1$ and $R^2$ is an alkoxycarbonyl group having more than 3 carbon atoms, and $R^3$ is a hydrogen group also can be prepared from compounds in which $R^3$ is a methyl group by treating with lithium thiomethoxide to remove the methyl group.

The present invention naphthylsulfonylalkanoic acid formula (I) compounds have one asymmetric carbon atom in the structure, and consequently exist in the form of two optical isomers. The configuration of substituents on the asymmetric carbon atom is not limited, and S-configuration, R-configuration or a mixture of S- and R-configurations can be employed in the present invention.

Naphthylsulfonylalkanoic acid formula (I) compounds in which $R^1$ and $R^2$ are the same or different and are an alkyl group or an alkoxy group, $R^3$ is a hydrogen atom, and n is 2 are preferred structures in the practice of the present invention embodiments.

Particularly preferred invention naphthylsulfonylalkanoic acid compounds include 4-[N-(3-methoxypropyl)-N-pentylcarbamoyl]-5-(2-naphthylsulfonyl)pentanoic acid, its optical isomers and the pharmaceutically acceptable salts thereof.

The compounds of formula (III) used as starting materials in the present invention are novel compounds and can be prepared by reacting 2-naphthalenethiol with compounds represented by the formula:

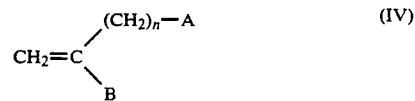

where (1) A and B are the same and are a cyano group or an alkoxycarbonyl group having 2 to 5 carbon atoms, or (2) A represents an alkoxycarbonyl group having 2 to 5 carbon atoms and B represents a carboxy group or alkali metal salts thereof, and n is as previously defined, in the presence of a Lewis-base or Lewis-acid to form a product represented by the formula:

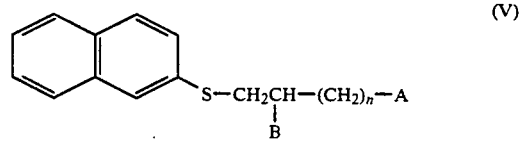

wherein A, B and n are as previously defined.

As a further alternative, hydrolyzing and then monoesterifying the product provides a compound represented by the formula:

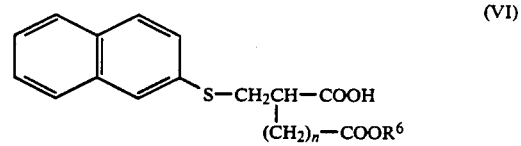

where $R^6$ and n are as previously defined. The compound of formula (VI) or a reactive functional derivative thereof subsequently can be reacted with an amino compound represented by the formula:

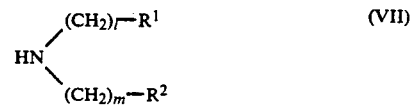

wherein $R^1$, $R^2$, l and m are as previously defined, to provide a selected compound of formula (III).

A synthesis procedure of the present invention can be conducted by dissolving a compound of formula (III) in a suitable organic solvent such as dichloromethane, then adding a molar excess(e.g., a 2.5 molar ratio) of an oxidizing agent such as m-chloroperbenzoic acid to the solution with cooling, stirring the reaction mixture for 2-3 hours with cooling or at room temperature, and working up the reaction mixture in accordance with standard methods to yield compounds of formula (I) wherein $R^3$ is a lower alkyl group or a benzyl group. Hydrolysis or hydrogenolysis of an ester product provides a compound of formula (I) in which $R^3$ is a hydrogen atom.

The compound of formula (I) in which $R^3$ is a hydrogen atom can be converted to pharmaceutically acceptable salts using standard procedures. Present invention salts include inorganic base salts such as a sodium salt or a calcium salt, and organic salts which are formed with bases such as morpholine, piperidine, arginine, and the like.

Salt compounds of the present invention exhibit a similar antagonistic activity toward CCK receptors as the corresponding free carboxylic acid compounds, and thus they are useful as therapeutic agents for the prevention or treatment of irritable bowel syndrome, biliary dyskinesia and acute pancreatitis.

When the naphthylsulfonylalkanoic acid compounds of formula (I) of the present invention or the pharmaceutically acceptable salts thereof are employed therapeutically, they can be administered in various dosage forms depending upon the intended therapy. Typical dosage forms which can be used are tablets, pills, powders, granules, capsules and injectable preparations. These pharmaceutical compositions can be formulated in accordance with standard molding procedures.

The dosage of the naphthylsulfonylalkanoic acid compounds of the present invention may be in the range from about 1 to 1000 mg per adult human by oral administration per day, or from about 0.1 to 100 mg per adult human by parenteral administration per day in multiple doses depending upon the type of disease, the severity of the condition to be treated, and the like.

The present invention is further illustrated in more detail by way of the following Examples and Reference Examples. The melting points of the products obtained are uncorrected.

REFERENCE EXAMPLE 1

2-(2-Methoxycarbonylethyl)-3-(2-naphthylthio)propionic acid

A mixture of 2-naphthalenethiol (10.0 g), 2-methyleneglutaronitrile (6.8 ml), ethanol (150 ml), and triton B (40% methanol solution, 10 drops) was refluxed for 2 hours. After the reaction mixture was concentrated in vacuo, the resulting residue was dissolved in chloroform, washed with water, and dried over $MgSO_4$. The solvent was evaporated at reduced pressure, and the residue was recrystallized from ethyl acetate-hexane to give 15.6 g of 2-(2-naphthylthiomethyl)-glutaronitrile.

Melting point: 52°-55° C.

| Elemental Analysis (for $C_{16}H_{14}N_2S$): | | | |
|---|---|---|---|
| | C % | H % | N % |
| Calcd. | 72.15 | 5.30 | 10.52 |
| Found | 71.98 | 5.24 | 10.41 |

IR (KBr): $\nu_{CN}$ 2245 cm$^{-1}$.

NMR (CDCl$_3$) δ: 1.95-2.3(2 H, m), 2.4-2.7(2 H, m), 2.8-2.95(1 H, m), 3.13(1 H, dd, J=7.1, 13.7 Hz), 3.30(1 H, dd, J=6.6, 13.7 Hz), 7.4-7.63(3 H, m), 7.75-8.0(4 H, m).

To a solution of 2-(2-naphthylthiomethyl)glutaronitrile (15.5 g) in acetic acid (70 ml) was added a concentrated hydrochloric acid (70 ml), and the mixture was refluxed for 17 hours. After the reaction mixture was concentrated in vacuo, diethyl ether was added, and the precipitates formed were filtered off. The filtrate was washed with water, and shaked with a saturated sodium bicarbonate solution. The aqueous layer was acidified with a concentrated hydrochloric acid, and extracted with diethyl ether. The organic layer was washed with water, dried over $MgSO_4$, and evaporated at reduced pressure. The residue was recrystallized from diethyl ether-hexane to give 15.9 g of 2-(2-naphthylthiomethyl)glutaric acid.

Melting point: 140°-142° C.

| Elemental Analysis (for $C_{16}H_{16}O_4S$): | | |
|---|---|---|
| | C % | H % |
| Calcd. | 63.14 | 5.30 |
| Found | 63.37 | 5.34 |

IR (KBr): $\nu_{C=O}$ 1720 cm$^{-1}$.

NMR (DMSO-d$_6$) δ: 1.7-2.0(2 H, m), 2.15-2.4(2 H, m), 2.5-2.65(1 H, m), 3.1-3.4(2 H, m), 7.35-7.6(3 H, m), 7.75-8.0(4 H, m), 12.32(2 H, s).

A mixture of 2-(2-naphthylthiomethyl)glutaric acid (28.8 g), methanol (300 ml), and p-toluenesulfonic acid (0.9 g) was stirred at 40° C. for 2.5 hours. The reaction mixture was concentrated in vacuo, and water was added to the resulting residue. The mixture was extracted with ethyl acetate, washed with water, dried over $MgSO_4$, and concentrated in vacuo. The residue was recrystallized from isopropyl ether to give 27.4 g of 2-(2-methoxycarbonylethyl)-3-(2-naphthylthio)propionic acid.

Melting point: 70°-71° C.

| Elemental Analysis (for $C_{17}H_{18}O_4S$): | | |
|---|---|---|
| | C % | H % |
| Calcd. | 64.13 | 5.70 |
| Found | 64.11 | 5.50 |

IR (KBr): $\nu_{C=O}$ 1730, 1700 cm$^{-1}$.

NMR (CDCl$_3$) δ: 1.95-2.2(2 H, m), 2.3-2.5(2 H, m), 2.65-2.8(1 H, m), 3.10(1 H, dd, J=6.6, 13.2 Hz), 3.33(1 H, dd, J=7.7, 13.2 Hz), 3.62(3 H, s), 7.4-7.55(3 H, m), 7.7-7.9(4 H, m).

REFERENCE EXAMPLE 2

(+)-2-(2-Methoxycarbonylethyl)-3-(2-naphthylthio)propionic acid and
(-)-2-(2-methoxycarbonylethyl)-3-(2-naphthylthio)propionic acid A mixture of (±)-2-(2-methoxycarbonylethyl)-3-(2-naphthylthio)propionic acid (10.00 g), ethanol (20 ml), and methanol (5 ml) was heated to solution, and (+)-1-phenylethylamine (3.80 g) was added. This solution was allowed to stand at room temperature. The precipitated crystals were collected, and further dissolved in ethanol (9 ml) and methanol (3 ml) by heating. After standing at room temperature, the crystals were collected by filtration to obtain 2.88 g of the salt formed from (+)-2-(2-methoxycarbonylethyl)-3-(2-naphthylthio)propionic acid and (+)-1-phenylethylamine. To this salt (0.72 g) was added a 2N hydrochloric acid (10 ml), and a separated oil was extracted with ethyl acetate. The organic layer was washed with water, dried over MgSO4, and evaporated at reduced pressure. The resulting residue was recrystallized from isopropyl ether to give 0.37 g of (+)-2-(2-methoxycarbonylethyl)-3-(2-naphthylthio)-propionic acid.

Melting point: 72°–74° C.
Specific rotation: $[\alpha]_D$ +46.8° (C=1.50, MeOH).
IR (KBr): $\nu_{C=O}$ 1740, 1725, 1690 cm$^{-1}$.
NMR (CDCl3): The same spectrum as those of the racemate.

In a further step, the above first filtrate was concentrated in vacuo, and the resulting residue was recrystallized three times from ethanol to give 1.04 g of the salt formed from (−)-2-(2-methoxycarbonylethyl)-3-(2-naphthylthio)propionic acid and (+)-1-phenylethylamine. To this salt (0.90 g) was added a 2N hydrochloric acid (15 ml), and a separated oil was extracted with ethyl acetate. The organic layer was washed with water, dried over MgSO4, and evaporated at reduced pressure. The residue was recrystallized from isopropyl ether to give 0.46 g of (−)-2-(2-methoxycarbonylethyl)-3-(2-naphthylthio)propionic acid.

Specific rotation: $[\alpha]_D$ −45.6° (C=1.07, MeOH).
Melting point, IR spectrum and NMR spectrum were the same as those of the (+)-isomer.

REFERENCE EXAMPLE 3

2-(2-Benzyloxycarbonylethyl)-3-(2-naphthylthio)propionic acid

To a solution of 2-(2-naphthylthiomethyl)glutaric acid (14.0 g) in acetonitrile (180 ml) was added benzyl alcohol (57 ml) followed by p-toluenesulfonic acid (0.52 g), and the mixture was refluxed for 23 hours. The reaction mixture was concentrated in vacuo, and the resulting residue was purified by flash column chromatography on silica eluting with dichloromethane/methanol (70:1), and recrystallized from ethyl acetate-hexane to give 11.0 g of 2-(2-benzyloxycarbonylethyl)-3-(2-naphthylthio)propionic acid.

Melting point: 94°–95° C.
Elemental Analysis (for C23H22O4S):

| | C % | H % |
|---|---|---|
| Calcd. | 70.03 | 5.62 |
| Found | 70.05 | 5.69 |

IR (KBr): $\nu_{C=O}$ 1730, 1700 cm$^{-1}$.
NMR (CDCl3) δ: 1.9–2.2(2 H, m), 2.3–2.55(2 H, m), 2.65–2.8(1 H, m), 3.09(1 H, dd, J=6.6, 13.2 Hz), 3.26(1 H, dd, J=7.7, 13.2 Hz), 5.09(2 H, s), 7.2–7.5(8 H, m), 7.65–7.85(4 H, m).

REFERENCE EXAMPLE 4

2-Methoxycarbonylmethyl-3-(2-naphthylthio)propionic acid

A mixture of 2-naphthalenethiol (0.38 g), sodium 3-methoxycarbonyl-2-methylenepropionate (0.39 g), methanol (20 ml), and triton B (40% methanol solution, 10 drops) was refluxed for 12 hours. The reaction mixture was concentrated in vacuo, and the resulting residue was acidified with a dilute hydrochloric acid, and extracted with ethyl acetate. The organic layer was washed with water, and dried over MgSO4. The solvent was evaporated at reduced pressure, and the residue was purified by medium pressure liquid column chromatography on silica eluting with chloroform/methanol (20:1), and recrystallized from isopropyl ether to give 0.38 g of 2-methoxycarbonylmethyl-3-(2-naphthylthio)propionic acid.

Melting point: 97°–99° C.

| Elemental Analysis (for C16H16O4S): | | |
|---|---|---|
| | C % | H % |
| Calcd. | 63.14 | 5.30 |
| Found | 63.12 | 5.27 |

IR (KBr): $\nu_{C=O}$ 1735, 1700 cm$^{-1}$.
NMR (CDCl3) δ: 2.7–2.9(2 H, m), 3.0–3.25(2 H, m), 3.47(1 H, dd, J=5.0, 13.2 Hz), 3.64(3 H, s), 7.4–7.55(3 H, m), 7.7–7.9(4 H, m).

REFERENCE EXAMPLE 5

Methyl 4-(N,N-dipentylcarbamoyl)-5-(2-naphthylthio)pentanoate

To a solution of 2-(2-methoxycarbonylethyl)-3-(2-naphthylthio)propionic acid (4.0 g) in dry dichloromethane (80 ml) was added thionyl chloride (4.0 ml), and the reaction mixture was refluxed for 2 hours. This solution was concentrated in vacuo. The residue was dissolved in dry dichloromethane (20 ml) and added dropwise into a solution of dipentylamine (3.5 ml) and triethylamine (5.4 ml) in dry dichloromethane (80 ml) with stirring at 0° C. After stirring at room temperature for 16 hours, the reaction mixture was washed with a dilute hydrochloric acid, water, a saturated sodium bicarbonate solution, and water respectively, dried over MgSO4, and concentrated in vacuo. The residue was purified by medium pressure liquid column chromatography on silica eluting with dichloromethane to give 5.1 g of methyl 4-(N,N-dipentylcarbamoyl)-5-(2-naphthylthio)pentanoate as oil.

IR (neat): $\nu_{C=O}$ 1735, 1640 cm$^{-1}$.
NMR (CDCl3) δ: 0.66(3 H, t, J=7.1 Hz), 0.8–1.05(7 H, m), 1.15–1.6(8 H, m), 2.0–2.5(4 H, m), 2.85–3.4(7 H, m), 3.63(3 H, s), 7.4–7.55(3 H, m), 7.7–7.85(4 H, m).

REFERENCE EXAMPLE 6

The compounds in the table were prepared in a similar manner to that described in reference example 5 (all compounds were oils). The compounds in which no specific rotation shows are in a racemate.

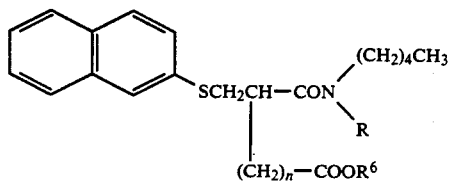

| R | R[6] | n | Specific rotation [α]$_D$ | IR (cm$^{-1}$) | NMR (δ, CDCl$_3$) |
|---|---|---|---|---|---|
| 3-methoxy-propyl | methyl | 2 | | 1735, 1635 (C=O) | 0.6–1.05(5H, m), 1.15–1.85(6H, m), 2.0–2.5(4H, m), 2.9–3.45(12H, m), 3.63(3H, s), 7.35–7.55(3H, m), 7.7–7.85(4H, m) |
| 3-methoxy-propyl | methyl | 2 | +106.8° (C=0.83, MeOH) | | the same as mentioned above |
| 3-methoxy-propyl | methyl | 2 | −108.4° (C=1.05, MeOH) | | the same as mentioned above |
| ethoxy-carbonylmethyl | benzyl | 2 | | 1735, 1650 (C=O) | 0.6–1.5(12H, m), 1.95–2.6(4H, m), 2.8–3.45(5H, m), 3.75 and 3.80(1H, d, J=17.0Hz), 3.96 and 4.16(2H, q, J=7.1Hz), 3.98 and 4.21(1H, d, J=17.0Hz), 5.07 and 5.09(2H, s), 7.2–7.55(8H, m), 7.7–7.85(4H, m) |
| ethoxy-carbonylmethyl | methyl | 2 | | 1735, 1645 (C=O) | 0.6–1.5(12H, m), 1.95–2.55(4H, m), 2.8–3.5(5H, m), 3.61 and 3.63(3H, s), 3.7–4.3(4H, m), 7.35–7.55 3H, m), 7.7–7.85(4H, m) |
| 2-ethoxy-carbonylethyl | benzyl | 2 | | 1735, 1635 (C=O) | 0.6–1.6(12H, m), 1.95–2.65(6H, m), 2.9–3.65(7H, m), 3.85–4.15(2H, m), 5.09(2H, s), 7.2–7.55(8H, m), 7.65–7.85(4H, m) |
| isopropoxy-carbonylmethyl | benzyl | 2 | | 1735, 1645 (C=O) | 0.55–1.65(15H, m), 2.0–2.6(4H, m), 2.8–3.45(5H, m), 3.72 and 3.78(1H, d, J=17.3Hz), 3.99 and 4.18(1H, d, J=17.3Hz), 4.8–5.15(3H, m), 7.2–7.5(8H, m), 7.65–7.85(4H, m) |
| tert-butoxy-carbonylmethyl | methyl | 2 | | 1740, 1645 (C=O) | 0.6–1.65(18H, m), 2.0–2.55(4H, m), 2.75–3.45(5H, m), 3.62 and 3.63(3H, s), 3.69 and 3.71(1H, d, J=17.3Hz), 3.96 and 4.09(1H, d, J=17.3Hz), 7.4–7.55(3H, m), 7.7–7.85(4H, m) |
| tert-butoxy-carbonylmethyl | methyl | 2 | +80.1° (C=1.39, MeOH) | | the same as mentioned above |
| N,N-diethyl-carbamoylmethyl | methyl | 2 | | 1735, 1645 (C=O) | 0.6–1.55(15H, m), 1.95–2.6(4H, m), 2.95–3.55(9H, m), 3.61 and 3.62(3H, s), 3.71 and 3.79(1H, d, J=15.3Hz), 3.96 and 4.27(1H, d, J=15.3Hz), 7.35–7.55 (3H, m), 7.7–7.85(4H, m) |
| N-isopropyl-carbamoylmethyl | methyl | 2 | | 3310 (NH) 1735, 1645 (C=O) | 0.6–1.45(15H, m), 1.95–2.5(4H, m), 3.0–4.3(11H, m), 6.25 and 6.55(1H, brs), 7.35–7.55(3H, m), 7.7–7.85(4H, m) |
| N-cyclohexyl-carbamoylmethyl | methyl | 2 | | 3310 (NH) 1740, 1650 (C=O) | 0.55–2.55(23H, m), 3.0–3.4(5H, m), 3.55–4.3(6H, m), 6.2 and 6.6(1H, brs), 7.35–7.55(3H, m), 7.7–7.85 (4H, m) |
| pentyl | methyl | 1 | | 1735, 1640 (C=O) | 0.65(3H, t, J=6.9Hz), 0.7–1.05(7H, m), 1.15–1.55 (8H, m), 2.83(2H, d, J=6.4Hz), 2.85–3.35(7H, m), 3.67(3H, s), 7.4–7.55(3H, m), 7.7–7.9(4H, m) |

REFERENCE EXAMPLE 7

Methyl 4-[N,N-bis(2-cyclohexylethyl)carbamoyl]-5-(2-naphthylthio)pentanoate

To a solution of 2-(2-methoxycarbonylethyl)-3-(2-naphthylthio)propionic acid (0.64 g) in dry dichloromethane (10 ml) was added thionyl chloride (0.3 ml), and the mixture was refluxed for 2 hours. The reaction mixture was concentrated in vacuo, and the residue which was dissolved in dry dichloromethane (5 ml) was added dropwise into a solution of bis(2-cyclohexylethyl)amine (0.48 g) and triethylamine (0.7 ml) in dry dichloromethane (15 ml) with stirring at 0° C. After stirring at room temperature for 20 hours, the reaction mixture was washed with a dilute hydrochloric acid, a saturated sodium bicarbonate solution, and water respectively, dried over MgSO$_4$, and concentrated in vacuo. The residue was purified by medium pressure liquid column chromatography on silica eluting with ethyl acetate/hexane (1:2) to give 0.94 g of methyl 4-[N,N-bis(2-cyclohexylethyl)carbamoyl]-5-(2-naphthylthio)pentanoate as oil.

IR (neat): $\nu_{C=O}$ 1735, 1635 cm$^{-1}$:

NMR (CDCl$_3$) δ: 0.3–1.75(26 H, m), 2.0–2.5(4 H, m), 2.85–3.4(7 H, m), 3.65(3 H, s), 7.35–7.55(3 H, m), 7.7–7.85(4 H, m).

REFERENCE EXAMPLE 8

The compounds in the table were prepared in a similar manner to that described in reference example 7 (all compounds were oils).

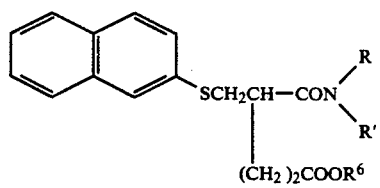

| R | R' | R[6] | IR (cm$^{-1}$) | NMR (δ, CDCl$_3$) |
|---|---|---|---|---|
| 2-acetoxy-ethyl | 2-acetoxy-ethyl | benzyl | 1735, 1645 (C=O) | 1.89(3H, s), 1.95–2.15(5H, m), 2.3–2.55(2H, m), 3.0–3.7(7H, m), 3.85–4.25(4H, m), 5.08(2H, s), 7.25–7.5(8H, m), 7.7–7.85(4H, m) |
| ethoxy- | ethoxy- | benzyl | 1740, 1655 | 1.07(3H, t, J=7.1Hz), 1.25(3H, t, J=7.1Hz), 2.0–2.55 |

-continued

| R | R' | R⁶ | IR (cm⁻¹) | NMR (δ, CDCl₃) |
|---|---|---|---|---|
| carbonylmethyl | carbonylmethyl |  | (C=O) | (4H, m), 2.9-3.15(2H, m), 3.33(1H, dd, J=6.6, 13.2Hz), 3.85-4.25(8H, m), 5.06(2H, s), 7.25-7.55 (8H, m), 7.7-7.85(4H, m) |
| 2-allyloxy-ethyl | 2-allyloxy-ethyl | methyl | 1735, 1635 (C=O) | 2.0-2.45(4H, m), 3.05-4.0(18H, m), 5.0-5.3(4H, m), 5.71(1H, ddt, J=9.9, 17.0, 5.5Hz), 5.87(1H, ddt, J=9.9, 17.0, 5.5Hz), 7.35-7.55(3H, m), 7.7-7.85(4H, m) |
| 3-methoxy-propyl | ethoxy-carbonylmethyl | benzyl | 1735, 1645 (C=O) | 1.08 and 1.24(3H, t, J=7.1Hz), 1.45-1.8(2H, m), 2.0-2.2(2H, m), 2.3-2.6(2H, m), 2.8-3.55(10H, m), 3.7-4.3(4H, m), 5.06 and 5.09(2H, s), 7.25-7.55(8H, m), 7.7-7.85(4H, m) |

REFERENCE EXAMPLE 9

Benzyl 4-[N-(2-acetoxyethyl)-N-pentylcarbamoyl]-5-(2-naphthylthio)pentanoate To a solution of 2-(2-benzyloxycarbonylethyl)-3-(2-naphthylthio)propionic acid (0.40 g) in dry dichloromethane (5 ml) was added thionyl chloride (0.15 ml), and the mixture was refluxed for 3 hours. After the reaction mixture was concentrated in vacuo, the residue which was dissolved in dry dichloromethane (5 ml) was added dropwise into a solution of N-(2-acetoxyethyl)-N-pentylamine hydrochloride (0.21 g) and triethylamine (0.42 ml) in dry dichloromethane (10 ml) with stirring at 0° C. After stirring at room temperature for 16 hours, the reaction mixture was washed with a dilute hydrochloric acid, water, a saturated sodium bicarbonate solution, and water respectively, dried over MgSO₄, and concentrated in vacuo. The residue was purified by flash column chromatography on silica eluting with ethyl acetate/hexane (1:1) to give 0.53 g of benzyl 4-[N-(2-acetoxyethyl)-N-pentylcarbamoyl]-5-(2-naphthylthio)pentanoate as oil.

IR (neat): $\nu_{C=O}$ 1735, 1640 cm⁻¹.
NMR (CDCl₃)
δ: 0.55-1.55(9 H, m), 1.85-2.55(7 H, m), 2.9-4.25(9 H, m), 5.09(2 H, s), 7.25-7.55(8 H, m), 7.7-7.85(4 H, m).

REFERENCE EXAMPLE 10

The compounds in the table were prepared in a similar manner to that described in reference example 9 (all compounds were oils).

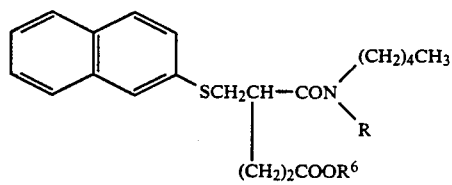

EXAMPLE 1

Methyl 4-(N-tert-butoxycarbonylmethyl-N-pentylcarbamoyl)-5-(2-naphthylsulfonyl)pentanoate (Compound No. 1)

Into a solution of methyl 4-(N-tert-butoxycarbonylmethyl-N-pentylcarbamoyl)-5-(2-naphthylthio)pentanoate (2.96 g) in dry dichloromethane (100 ml) was added by portions of m-chloroperbenzoic acid (80%, 3.67 g) with stirring at 0° C. After stirring at room temperature for 4 hours, sodium sulfite was added. The reaction mixture was washed with a saturated sodium bicarbonate solution and water, dried over MgSO₄, and concentrated in vacuo. The residue was purified by flash column chromatography on silica eluting with ethyl acetate/hexane (1:2), and recrystallized from isopropyl ether-hexane to give 2.97 g of methyl 4-(N-tert-butoxycarbonylmethyl-N-pentylcarbamoyl)-5-(2-naphthylsulfonyl)pentanoate.

Melting point: 85°-87° C.

| Elemental Analysis (for C₂₈H₃₉NO₇S): | | | |
|---|---|---|---|
|  | C % | H % | N % |
| Calcd. | 63.02 | 7.37 | 2.62 |
| Found | 62.75 | 7.24 | 2.37 |
| IR (KBr): $\nu_{C=O}$ 1730, 1650 cm⁻¹ $\nu_{SO_2}$ 1310, 1170 cm⁻¹ | | | |

NMR (CDCl₃) δ: 0.85 and 0.90(3 H, t, J=7.1 Hz), 1.1-1.7(15 H, m), 1.85-2.45(4 H, m), 3.05-4.0(9 H, m), 4.07 and 4.29(1 H, d, J=16.5 Hz), 7.55-7.75(2 H, m), 7.8-8.05(4 H, m), 8.49(1 H, s).

EXAMPLE 2

The compounds in the table were prepared in a similar manner to that described in example 1. The compounds in which no specific rotation shows are in a racemate.

| R | R⁶ | IR (cm⁻¹) | NMR (δ, CDCl₃) |
|---|---|---|---|
| 2-pivaloyloxyethyl | benzyl | 1730, 1635 (C=O) | 0.6-1.65(18H, m), 2.0-2.55(4H, m), 2.9-3.65(7H, m), 3.85-4.25(2H, m), 5.08 and 5.09(2H, s), 7.2-7.55(8H, m), 7.7-7.85(4H, m) |
| 3-(2-oxo-1-pyrrolidinyl)propyl | methyl | 1730, 1680, 1630 (C=O) | 0.6-2.5(19H, m), 2.75-3.45(11H, m), 3.64 and 3.66 (3H, s), 7.35-7.55(3H, m), 7.7-7.85(4H, m) |
| tert-butoxycarbonylmethyl | methyl | 1740, 1645 (C=O) | 0.6-1.65(18H, m), 2.0-2.55(4H, m), 2.75-3.45(5H, m), 3.62 and 3.63(3H, s), 3.69 and 3.71(1H, d, J=17.3Hz), 3.96 and 4.09(1H, d, J=17.3Hz), 7.4-7.55(3H, m), 7.7-7.85(4H, m) |

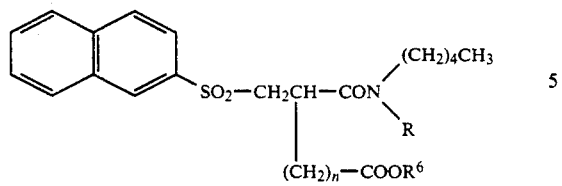

5

10

| No. | R | R⁶ | n | mp (°C.) (recryst. solvent) | Specific rotation $[\alpha]_D$ | IR (cm⁻¹) | NMR (δ, CDCl₃) |
|---|---|---|---|---|---|---|---|
| 2 | pentyl | methyl | 2 | 72–73 (hexane) | | 1725, 1635 (C=O) 1310, 1170 (SO₂) | 0.86(3H, t, J=7.1Hz), 0.92(3H, t, J=7.1Hz), 1.1–1.7(12H, m), 1.85–2.1(2H, m), 2.33(2H, t, J=7.1Hz), 3.0–3.5(6H, m), 3.63(3H, s), 3.84(1H, dd, J=8.2, 14.3Hz), 7.6–7.75(2H, m), 7.85–8.05(4H, m), 8.48(1H, s) |
| 3 | 3-methoxy-propyl | methyl | 2 | 55.5–57.5 (isopropyl ether-hexane) | | 1730, 1620 (C=O) 1300, 1140 (SO₂) | 0.86 and 0.92(3H, t, J=6.9Hz), 1.1–2.1(10H, m), 2.25–2.4(2H, m), 3.0–3.5(11H, m), 3.63 and 3.64 (3H, s), 3.84 and 3.90(1H, dd, J=7.9, 13.9Hz), 7.55–7.7(2H, m), 7.8–8.05(4H, m), 8.48(1H, s) |
| 4 | 3-methoxy-propyl | methyl | 2 | oil | +9.4° (C=1.15, MeOH) | 1730, 1630 (C=O) 1305, 1150 (SO₂) | the same as mentioned above |
| 5 | 3-methoxy-propyl | methyl | 2 | oil | −9.3° (C=1.14, MeOH) | | the same as mentioned above |
| 6 | ethoxy-carbonylmethyl | benzyl | 2 | 79–81 (diethyl ether-hexane) | | 1745, 1715, 1635 (C=O) 1325, 1145 (SO₂) | 0.85 and 0.89(3H, t, J=6.9Hz), 1.1–1.7(9H, m), 1.9–2.2(2H, m), 2.35–2.55(2H, m), 3.1–4.4(9H, m), 5.0–5.2(2H, m), 7.2–7.4 (5H, m), 7.6–7.75(2H, m), 7.8–8.05(4H, m), 8.49(1H, s) |
| 7 | ethoxy-carbonylmethyl | methyl | 2 | 84–85 (isopropyl ether) | | 1730, 1645 (C=O) 1305, 1170 (SO₂) | 0.85 and 0.90(3H, t, J=7.1Hz), 1.1–1.7(9H, m), 1.8–2.5(4H, m), 3.1–4.45(12H, m), 7.6–7.75(2H, m), 7.8–8.05(4H, m), 8.49(1H, s) |
| 8 | 2-ethoxy-carbonylethyl | benzyl | 2 | oil | | 1735, 1640 (C=O) 1310, 1155 (SO₂) | 0.86 and 0.91(3H, t, J=6.9Hz), 1.1–1.7(9H, m), 1.8–2.15(2H, m), 2.3–2.85(4H, m), 3.0–3.75(6H, m), 3.81 and 3.90(1H, dd, J=7.9, 13.8Hz), 4.09 and 4.17(2H, q, J=6.9Hz), 5.0–5.15(2H, m), 7.2–7.45(5H, m), 7.6–7.75(2H, m), 7.8–8.05(4H, m), 8.47(1H, s) |
| 9 | isopropoxy-carbonylmethyl | benzyl | 2 | oil | | 1730, 1640 (C=O) 1305, 1155 (SO₂) | 0.85 and 0.89(3H, t, J=7.1Hz), 1.1–1.6(12H, m), 1.9–2.5(4H, m), 3.1–4.05(6H, m), 4.16 and 4.32 (1H, d, J=17.0Hz), 4.95–5.15(3H, m), 7.2–7.4(5H, m), 7.55–7.75 (2H, m), 7.8–8.05(4H, m), 8.49 (1H, s) |
| 10 | tert-butoxy-carbonylmethyl | methyl | 2 | oil | +7.2° (C=1.28, MeOH) | 1735, 1640 (C=O) 1310, 1155 (SO₂) | the agreement with example 1 |
| 11 | N,N-diethyl-carbamoylmethyl | methyl | 2 | oil | | 1730, 1640 (C=O) 1305, 1145 (SO₂) | 0.87 and 0.91(3H, t, J=6.9Hz), 1.0–1.75(12H, m), 1.9–2.5(4H, m), 3.1–3.65(12H, m), 3.73 and 3.84 (1H, dd, J=6.9, 13.9Hz), 4.14 and 4.47(1H, d, J=17.3Hz), 7.6–7.75 (2H, m), 7.85–8.1(4H, m), 8.49 (1H, s) |
| 12 | N-isopropyl-carbamoylmethyl | methyl | 2 | oil | | 3380 (NH) 1730, 1650 (C=O) 1305, 1150 (SO₂) | 0.89 and 0.93(3H, t, J=6.6Hz), 1.05–2.45(16H, m), 3.0–4.25 (10H, m), 4.34 and 4.65(1H, d, J=17.0Hz), 6.85 and 6.97(1H, d, J=7.7Hz), 7.6–8.1(6H, m), 8.48 (1H, s) |
| 13 | N-cyclohexyl-carbamoylmethyl | methyl | 2 | 116–117.5 (isopropyl ether-hexane) | | 3360 (NH) 1730, 1645, 1630 (C=O) 1310, 1170 | 0.89 and 0.93(3H, t, J=6.6Hz), 1.0–2.45(20H, m), 3.0–4.15(10H, m), 4.34 and 4.60(1H, d, J=16.5Hz), 6.83 and 6.93(1H, d, J=8.2Hz), 7.6– |

| No. | R | R⁶ | n | mp (°C.) (recryst. solvent) | Specific rotation [α]$_D$ | IR (cm⁻¹) | NMR (δ, CDCl₃) |
|---|---|---|---|---|---|---|---|
| 14 | pentyl | methyl | 1 | oil | | (SO₂) 1735, 1640 (C=O) 1315, 1150 (SO₂) | 8.1(6H, m), 8.48(1H, s) 0.86(3H, t, J=7.1Hz), 0.88(3H, t, J=7.1Hz), 1.05–1.7(12H, m), 2.85 (2H, d, J=7.1Hz), 3.1–3.3(4H, m), 3.34(1H, dd, J=7.7, 14.3Hz), 3.50 (1H, dd, J=5.5, 14.3Hz), 3.6–3.8 (4H, m), 7.6–7.75(2H, m), 7.85–8.05(4H, m), 8.50(1H, s) |

EXAMPLE 3

N-[2-(2-Methoxycarbonylethyl)-3-(2-naphthylsulfonyl)propionyl]-N-pentylglycine (Compound No. 15)

Methyl 4-(N-tert-butoxycarbonylmethyl-N-pentylcarbamoyl)-5-(2-naphthylsulfonyl)pentanoate (0.47 g) was dissolved in trifluoroacetic acid (5 ml) at 0° C., and stirred at room temperature for 2 hours. After the reaction mixture was concentrated in vacuo, the resulting residue was purified by flash column chromatography on silica eluting with chloroform/methanol (15:1) to give 0.34 g of N-[2-(2-methoxycarbonylethyl)-3-(2-naphthylsulfonyl)propionyl]-N-pentylglycine as an amorphous solid.

IR (KBr): $v_{C=O}$ 1725, 1630 cm⁻¹
$v_{SO_2}$ 1305, 1140 cm⁻¹

NMR (CDCl₃) δ: 0.86 and 0.92(3 H, t, J=7.1 Hz), 1.1–2.45(10 H, m), 3.1–3.9(9 H, m), 4.13 and 4.42(1 H, d, J=16.5 Hz), 7.6–8.1(6 H, m), 8.48(1 H, s).

EXAMPLE 4

Methyl 4-[N-(N,N-dimethylcarbamoylmethyl)-N-pentylcarbamoyl]-5-(2-naphthylsulfonyl)pentanoate (Compound No. 16)

To a solution of N-[2-(2-methoxycarbonylethyl)-3-(2-naphthylsulfonyl)propionyl]-N-pentylglycine (100 mg), dimethylamine hydrochloride (21 mg), and triethylamine (70 μl) in N,N-dimethylformamide (1 ml) was added diethyl cyanophosphonate (42 μl) at 0° C. After stirring at room temperature for 16 hours, a dilute hydrochloric acid was added, and the reaction mixture was extracted with ethyl acetate. The organic layer was washed with a saturated sodium bicarbonate solution and water, dried over MgSO₄, and evaporated at reduced pressure. The residue was purified by flash column chromatography on silica eluting with chloroform/methanol (15:1) to give 95 mg of methyl 4-[N-(N,N-dimethylcarbamoylmethyl)-N-pentylcarbamoyl]-5-(2-naphthylsulfonyl)-pentanoate as oil.

IR (neat): $v_{C=O}$ 1735, 1650 cm⁻¹
$v_{SO_2}$ 1310, 1150 cm⁻¹

NMR (CDCl₃) δ: 0.88 and 0.90(3 H, t, J=6.6 Hz), 1.15–1.7(6 H, m), 1.95–2.5(4 H, m), 2.90, 2.91, 2.97 and 3.02(6 H, s), 3.1–4.15(9 H, m), 4.23 and 4.42(1 H, d, J=15.9 Hz), 7.55–7.75(2 H, m), 7.85–8.05(4 H, m), 8.50(1 H, s).

EXAMPLE 5

In a similar manner to that described in example 4, the following compound was prepared.

Methyl 4-[N-(N,N-diisopropylcarbamoylmethyl)-N-pentylcarbamoyl]-5-(2-naphthylsulfonyl)pentanoate (Compound No. 17)

Property: oil.

IR (neat): $v_{C=O}$ 1730, 1640 cm⁻¹
$v_{SO_2}$ 1305, 1150 cm⁻¹

NMR (CDCl₃) δ: 0.8–2.5(25 H, m), 3.1–4.5(12 H, m), 7.6–8.1(6 H, m), 8.46 and 8.50(1 H, s).

EXAMPLE 6

4-[N-(3-Methoxypropyl)-N-pentylcarbamoyl]-5-(2-naphthylsulfonyl)pentanoic acid (Compound No. 18)

To a solution of methyl 4-[N-(3-methoxypropyl)-N-pentylcarbamoyl]-5-(2-naphthylsulfonyl)pentanoate (2.50 g) in ethanol (30 ml) was added a 1N sodium hydroxide solution (5.1 ml). After stirring at room temperature for 16 hours, the reaction mixture was concentrated in vacuo, acidified with a dilute hydrochloric acid, and extracted with ethyl acetate. The organic layer was washed with water, dried over MgSO₄, and evaporated at reduced pressure. The residue was recrystallized from isopropyl ether to give 2.15 g of 4-[N-(3-methoxypropyl)-N-pentylcarbamoyl]-5-(2-naphthylsulfonyl)pentanoic acid.

Melting point: 79°–82° C.

| Elemental Analysis (for C₂₅H₃₅NO₆S): | | | |
|---|---|---|---|
| | C % | H % | N % |
| Calcd. | 62.87 | 7.39 | 2.93 |
| Found | 62.57 | 7.28 | 2.95 |

IR (KBr): $v_{C=O}$ 1720, 1625 cm⁻¹
$v_{SO_2}$ 1300, 1140 cm⁻¹

NMR (CDCl₃) δ: 0.86 and 0.90(3 H, t, J=7.1 Hz), 1.1–2.15(10 H, m), 2.38(2 H, t, J=6.6 Hz), 3.0–3.55(11 H, m), 3.75–3.95(1 H, m), 7.55–7.75(2 H, m), 7.8–8.05(4 H, m), 8.48(1 H, s).

EXAMPLE 7

4-(N-Ethoxycarbonylmethyl-N-pentylcarbamoyl)-5-(2-naphthylsulfonyl)pentanoic acid (Compound No. 19)

To a solution of benzyl 4-(N-ethoxycarbonylmethyl-N-pentylcarbamoyl)-5-(2-naphthylsulfonyl)pentanoate (200 mg) in ethanol (10 ml) was added 10% Pd-C (20 mg), and the mixture was hydrogenolyzed at atmospheric pressure for 60 hours. After the catalyst was filtered off, the filtrate was concentrated in vacuo. The residue was purified by flash column chromatography on silica eluting with chloroform/methanol (10:1), and recrystallized from isopropyl ether-hexane to give 170 mg of 4-(N-ethoxycarbonylmethyl-N-pentylcarbamoyl)-5-(2-naphthylsulfonyl)pentanoic acid.

Melting point: 77°–80° C.

| Elemental Analysis (for $C_{25}H_{35}NO_7S$): | | | |
|---|---|---|---|
| | C % | H % | N % |
| Calcd. | 61.08 | 6.77 | 2.85 |
| Found | 60.92 | 6.71 | 2.68 |

IR (KBr): $\nu_{C=O}$ 1735, 1690, 1630 cm$^{-1}$
$\nu_{SO_2}$ 1140 cm$^{-1}$

NMR (CDCl$_3$) δ: 0.86 and 0.89(3 H, t, J=7.1 Hz), 1.1–1.7(9 H, m), 1.85–2.2(2 H, m), 2.3–2.55(2 H, m), 3.1–4.1(6 H, m), 4.15 and 4.18(2 H, q, J=7.1 Hz), 4.22 and 4.40(1 H, d, J=17.0 Hz), 7.55–7.75(2 H, m), 7.8–8.05(4 H, m), 8.49(1 H, s)

EXAMPLE 8

The compounds in the table were prepared in a similar manner to that described in example 6 or 7. The compounds in which no specific rotation shows are in a racemate.

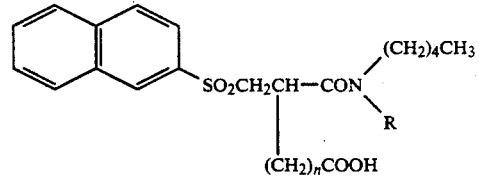

| No. | R | n | mp (°C.) (recryst. solvent) | Specific rotation [α]$_D$ | IR (cm$^{-1}$) | NMR (δ, CDCl$_3$) |
|---|---|---|---|---|---|---|
| 20 | pentyl | 2 | 88–90 (isopropyl ether-hexane) | | 1725, 1630 (C=O) 1305, 1145 (SO$_2$) | 0.86(3H, t, J=7.1Hz), 0.90(3H, t, J=7.1Hz), 1.1–1.7(12H, m), 1.85–2.15(2H, m), 2.38 (2H, t, J=7.1Hz), 3.0–3.5(6H, m), 3.83(1H, dd, J=7.7, 13.7Hz), 7.55–7.75(2H, m), 7.8–8.1(4H, m), 8.48(1H, s) |
| 21 | 2-ethoxy-carbonylethyl | 2 | 77–81 (isopropyl ether-hexane) | | 1730, 1700, 1625 (C=O) 1140 (SO$_2$) | 0.86 and 0.90(3H, t, J=7.1Hz), 1.1–2.1(11H, m), 2.3–3.95(11H, m), 4.11 and 4.17(2H, q, J=7.1Hz), 7.55–7.75(2H, m), 7.85–8.05 (4H, m), 8.48(1H, s) |
| 22 | 3-methoxy-propyl | 2 | 68–70 (isopropyl ether) | −24.5° (C=1.47, dioxane) | 1730, 1640 (C=O) 1305, 1150 (SO$_2$) | the agreement with example 6 |
| 23 | 3-methoxy-propyl | 2 | the same as above | +24.0° (C=1.40, dioxane) | | the same as mentioned above |
| 24 | isopropoxy-carbonylmethyl | 2 | 96.5–99.5 (isopropyl ether-hexane) | . | 1725, 1715, 1635 (C=O) 1300, 1140 (SO$_2$) | 0.86 and 0.89(3H, t, J=7.1Hz), 1.1–2.2(14H, m), 2.3–2.55(2H, m), 3.1–4.05(6H, m), 4.19 and 4.39(1H, d, J=17.0Hz), 4.95–5.1 (1H, m), 7.55–7.75(2H, m), 7.8–8.1(4H, m), 8.49(1H, s) |
| 25 | tert-butoxy-carbonylmethyl | 2 | 123–125 (diethyl ether-hexane) | | 1740, 1630 (C=O) 1310, 1160 (SO$_2$) | 0.86 and 0.89(3H, t, J=7.1Hz), 1.1–1.7(15H, m), 1.9–2.55(4H, m), 3.1–3.95(6H, m), 4.11 and 4.32(1H, d, J=17.0Hz), 7.55–7.75 (2H, m), 7.8–8.1(4H, m), 8.49(1H, s) |
| 26 | tert-butoxy-carbonylmethyl | 2 | 90–92 (isopropyl ether) | +1.3° (C=0.94, MeOH) | 1740, 1620, (C=O) 1310, 1155 (SO$_2$) | the same as mentioned above |
| 27 | N,N-dimethyl-carbamoylmethyl | 2 | amorphous | | 1725, 1635 (C=O) 1305, 1150 (SO$_2$) | (*) 0.92(3H, t, J=6.6Hz), 1.05–2.0(8H, m), 2.27 and 2.41(2H, t, J=7.1Hz), 2.7–4.4(13H, m), 7.7–8.4(6H, m), 8.66 and 8.69(1H, s), 12.2 (1H, brs) |
| 28 | N,N-diethyl-carbamoylmethyl | 2 | 83–87 (isopropyl ether-hexane) | | 1715, 1655, 1635 (C=O) 1305, 1160 (SO$_2$) | 0.87 and 0.89(3H, t, J=7.1Hz), 1.0–2.55 (16H, m), 3.0–4.15(10H, m), 4.42 and 4.59 (1H, d, J=15.9Hz), 7.55–7.75(2H, m), 7.8–8.1(4H, m), 8.48(1H, s) |
| 29 | N,N-diisopropyl-carbamoylmethyl | 2 | 108–110 (diethyl ether-hexane) | | 1705, 1650, 1630 (C=O) 1300, 1140 (SO$_2$) | 0.88 and 0.89(3H, t, J=6.9Hz), 1.0–2.5(22H, m), 3.0–4.2(8H, m), 4.46 and 4.54(1H, d, J= 15.8Hz), 7.5–8.05(6H, m), 8.47 and 8.49 (1H,s) |
| 30 | N-isopropyl-carbamoylmethyl | 2 | 114–117 (isopropyl ether-hexane) | | 3380 (NH) 1715, 1650 (C=O) 1305, 1150 (SO$_2$) | (*) 0.90 and 0.92(3H, t, J=7.1Hz), 1.0–1.65 (12H, m), 1.75–2.4(4H, m), 3.05–4.15(8H, m), 7.45–8.4(7H, m), 8.67(1H, s) |
| 31 | N-cyclohexyl-carbamoylmethyl | 2 | amorphous | | 3380 (NH) 1730, 1645 (C=O) 1305, 1150 (SO$_2$) | 0.8–2.1(21H, m), 2.2–2.5(2H, m), 3.0–4.7(8H, m), 6.87 and 7.07(1H, d, J=7.7Hz), 7.6–8.1(6H, m), 8.48(1H, s) |
| 32 | pentyl | 1 | oil | | 1725, 1635 (C=O) 1310, 1150 (SO$_2$) | 0.87(3H, t, J=6.6Hz), 0.88(3H, t, J=6.6Hz), 1.1–1.65(12H, m), 2.89(2H, d, J=6.6Hz), 3.0–3.45(5H, m), 3.51(1H, dd, J=6.0, 14.3Hz), 3.65—3.8(1H, m), 7.6–7.75(2H, m), 7.8– |

-continued

| No. | R | n | mp (°C.) (recryst. solvent) | Specific rotation [α]$_D$ | IR (cm$^{-1}$) | NMR (δ, CDCl$_3$) |
|---|---|---|---|---|---|---|
| 33 | carboxymethyl | 2 | 94-98 (ethyl acetate-hexane) | | 1700, 1630 (C=O) 1140 (SO$_2$) | 8.05(4H, m), 8.50(1H, s) (*) 0.7-2.5(13H, m), 2.8-4.4(7H, m), 7.5-8.3(6H, m), 8.60(1H, s), 12.44(2H, brs) |

(*) The data were obtained in DMSO-d$_6$

EXAMPLE 9

4-(N-Ethoxycarbonylmethyl-N-pentylcarbamoyl)-5-(2-naphthylsulfonyl)pentanoic acid (Compound No. 19)

To a solution of methyl 4-(N-ethoxycarbonylmethyl-N-pentylcarbamoyl)-5-(2-naphthylsulfonyl)pentanoate (50 mg) in dry hexamethylphosphoric triamide (0.3 ml) was added lithium thiomethoxide (5 mg) under argon. After stirring at room temperature for 30 minutes, a dilute hydrochloric acid was added, and the reaction mixture was extracted with ethyl acetate. The organic layer was washed with water, dried over MgSO$_4$, and evaporated at reduced pressure. The residue was purified by medium pressure liquid column chromatography on silica eluting with chloroform/methanol (9:1), and recrystallized from isopropyl ether-hexane to give 23 mg of 4-(N-ethoxycarbonylmethyl-N-pentylcarbamoyl)-5-(2-naphthylsulfonyl)pentanoic acid. The physical properties of this compound were identical to that of compound No. 19, which was prepared in example 7.

EXAMPLE 10

Methyl 4-[N,N-bis(2-cyclohexylethyl)carbamoyl]-5-(2-naphthylsulfonyl)pentanoate (Compound No. 34)

Into a solution of methyl 4-[N,N-bis(2-cyclohexylethyl)carbamoyl]-5-(2-naphthylthio)pentanoate (0.50 g) in dry dichloromethane (20 ml) was added by portions of m-chloroperbenzoic acid (80%, 0.51 g) with stirring at 0° C. After stirring at room temperature for 6 hours, sodium sulfite was added to the mixture. The reaction mixture was washed with a saturated sodium bicarbonate solution and water, dried over MgSO$_4$, and concentrated in vacuo. The residue was purified by medium pressure liquid column chromatography on silica eluting with ethyl acetate/hexane (1:2), and recrystallized from ethyl acetate-hexane to give 0.48 g of methyl 4-[N,N-bis(2-cyclohexylethyl)carbamoyl]-5-(2-naphthylsulfonyl)pentanoate.

Melting point: 115.5°-118° C.

| Elemental Analysis (for C$_{33}$H$_{47}$NO$_5$S): | | | |
|---|---|---|---|
| | C % | H % | N % |
| Calcd. | 69.56 | 8.31 | 2.46 |
| Found | 69.51 | 8.22 | 2.33 |
| IR (KBr): ν$_{C=O}$ 1740, 1625 cm$^{-1}$ | | | |
| ν$_{SO_2}$ 1310, 1170 cm$^{-1}$ | | | |

NMR (CDCl$_3$) δ: 0.75-2.1(28 H, m), 2.32(2 H, t, J=7.1 Hz), 2.95-3.45(6 H, m), 3.63(3 H, s), 3.84(1 H, dd, J=7.7, 13.7 Hz), 7.55-7.75(2 H, m), 7.8-8.1(4 H, m), 8.48(1 H, s)

EXAMPLE 11

The compounds in the table were prepared in a similar manner to that described in example 10.

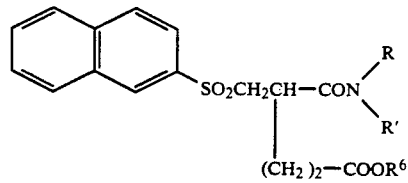

| No. | R | R' | R$^6$ | mp (°C.) (recryst. solvent) | IR (cm$^{-1}$) | NMR (δ, CDCl$_3$) |
|---|---|---|---|---|---|---|
| 35 | 2-acetoxyethyl | 2-acetoxyethyl | benzyl | 72-75 (diethyl ether-hexane) | 1745, 1735, 1715, 1630 (C=O) 1300, 1140 (SO$_2$) | 1.8-2.15(8H, m), 2.40(2H, t, J=6.9 Hz), 3.15(1H, dd, J=3.5, 13.9Hz), 3.4-3.8(5H, m), 3.84(1H, dd, J=8.4, 13.9 Hz), 4.18(2H, t, J=5.9Hz), 4.25(2H, t, J=5.9Hz), 5.06(1H, d, J=14.8Hz), 5.11(1H, d, J=14.8Hz), 7.2-7.4(5H, m), 7.6-7.75(2H, m), 7.8-8.05 (4H, m), 8.48(1H, s) |
| 36 | ethoxycarbonylmethyl | ethoxycarbonylmethyl | benzyl | oil | 1735, 1655 (C=O) 1315, 1150 (SO$_2$) | 1.22(3H, t, J=6.9Hz), 1.29(3H, t, J=6.9Hz), 1.9-2.2(2H, m), 2.35-2.55(2H, m), 3.19(1H, dd, J=5.4, 13.9Hz), 3.45-3.65(1H, m), 3.72 (1H, dd, J=6.4, 13.9Hz), 3.89(1H, d, J=17.8Hz), 4.0-4.25(6H, m), 4.34(1H, d, J=17.8Hz), 5.06(1H, d, J=15.3Hz), 5.11(1H, d, J=15.3Hz), 7.2-7.4(5H, m), 7.6-7.75(2H, m), 7.8-8.05 (4H, m), 8.51(1H, s) |
| 37 | 2-allyloxyethyl | 2-allyloxyethyl | methyl | oil | 1735, 1640 (C=O) 1310, 1150 (SO$_2$) | 1.85-2.1(2H, m), 2.34(2H, t, J=7.9Hz), 3.16(1H, dd, J=4.5, 13.9Hz), 3.35-4.0(17H, m), 5.1-5.3(4H, m), 5.75-6.0(2H, m), 7.6-7.75(2H, m), 7.85-8.05(4H, m), 8.48(1H, s) |

-continued

| No. | R | R' | R⁶ | mp (°C.) (recryst. solvent) | IR (cm⁻¹) | NMR (δ, CDCl₃) |
|---|---|---|---|---|---|---|
| 38 | 3-methoxy-propyl | ethoxy-carbonyl-methyl | benzyl | 67–69 (isopropyl ether-hexane) | 1740, 1710, 1630 (C=O) 1310, 1150 (SO₂) | 1.15–1.3(3H, m), 1.65–2.2(4H, m), 2.3–2.55(2H, m), 3.1–4.45(14H, m), 5.0–5.15(2H, m), 7.2–7.4 (5H, m), 7.55–7.7(2H, m), 7.8–8.05 (4H, m), 8.48(1H, s) |

EXAMPLE 12

4-[N,N-Bis(2-cyclohexylethyl)carbamoyl]-5-(2-naphthylsulfonyl)pentanoic acid (Compound No. 39)

To a solution of methyl 4-[N,N-bis(2-cyclohexylethyl)carbamoyl]-5-(2-naphthylsulfonyl)pentanoate (150 mg) in ethanol (3 ml) was added a 1N sodium hydroxide solution (0.26 ml), and the mixture was stirred at room temperature for 16 hours. The reaction mixture was concentrated in vacuo, acidified with a dilute hydrochloric acid, extracted with ethyl acetate. The organic layer was washed with water, dried over MgSO₄, and evaporated at reduced pressure. The residue was recrystallized from ethyl acetate-hexane to give 86 mg of 4-[N,N-bis(2-cyclohexylethyl)carbamoyl]-5-(2-naphthylsulfonyl)pentanoic acid.

Melting point: 138.5°–139.5° C.

| Elemental Analysis (for C₃₂H₄₅NO₅S): | | | |
|---|---|---|---|
| | C % | H % | N % |
| Calcd. | 69.16 | 8.16 | 2.52 |
| Found | 69.22 | 8.28 | 2.48 |
| IR (KBr): ν_{C=O} 1725, 1605 cm⁻¹ ν_{SO₂} 1300, 1150 cm⁻¹ | | | |

NMR (CDCl₃) δ: 0.7–2.1(28 H, m), 2.37(2 H, t, J=7.1 Hz), 3.0–3.5(6 H, m), 3.83(1 H, dd, J=7.7, 13.7 Hz), 7.55–7.75(2 H, m), 7.8–8.05(4 H, m), 8.48(1 H, s).

thoxycarbonylmethyl)carbamoyl]-5-(2-naphthylsulfonyl)pentanoic acid.

Melting point: 108°–111° C.

| Elemental Analysis (for C₂₄H₂₉NO₉S): | | | |
|---|---|---|---|
| | C % | H % | N % |
| Calcd. | 56.79 | 5.76 | 2.76 |
| Found | 56.56 | 5.87 | 2.52 |
| IR (KBr): ν_{C=O} 1730, 1705, 1645 cm⁻¹ ν_{SO₂} 1150 cm⁻¹ | | | |

NMR (CDCl₃) δ: 1.1–1.4(6 H, m), 1.9–2.55(4 H, m), 3.0–4.5(11 H, m), 7.5–7.75(2 H, m), 7.85–8.1(4 H, m), 8.51(1 H, s).

EXAMPLE 14

The compounds in the table were prepared in a similar manner to that described in example 12 or 13 (all compounds were oils).

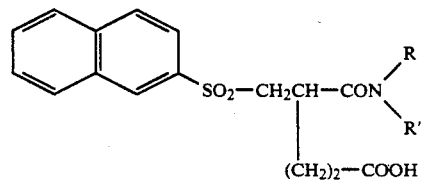

| No. | R | R' | IR (cm⁻¹) | NMR (δ, CDCl₃) |
|---|---|---|---|---|
| 41 | 2-allyloxyethyl | 2-allyloxyethyl | 1725, 1630 (C=O) 1300, 1140 (SO₂) | 1.8–2.45(4H, m), 3.23(1H, dd, J=3.8, 13.7Hz), 3.3–4.0(14H, m), 5.0–5.3(4H, m), 5.6–5.95(2H, m), 7.5–7.7(2H, m), 7.8–8.05(4H, m), 8.45(1H, s) |
| 42 | 3-methoxypropyl | ethoxycarbonyl-methyl | 1735, 1650 (C=O) 1305, 1150 (SO₂) | 1.24 and 1.29(3H, t, J=6.9Hz), 1.65–2.2(4H, m), 2.3–2.55(2H, m), 3.1–4.5(14H, m), 7.55–7.75(2H, m), 7.8–8.1(4H, m), 8.49(1H, s) |
| 43 | 2-acetoxyethyl | 2-acetoxyethyl | 1730, 1630 (C=O) 1305, 1145 (SO₂) | 1.7–2.5(10H, m), 3.0–3.25(1H, m), 3.4–3.95(6H, m), 4.15–4.35(4H, m), 7.55–7.75(2H, m), 7.8–8.1(4H, m), 8.48(1H, s) |

EXAMPLE 13

4-[N,N-Bis(ethoxycarbonylmethyl)carbamoyl]-5-(2-naphthylsulfonyl)pentanoic acid (Compound 40)

To a solution of benzyl 4-[N,N-bis(ethoxycarbonylmethyl)carbamoyl]-5-(2-naphthylsulfonyl)pentanoate (0.52 g) in ethanol (10 ml) was added 10% Pd-C (50 mg), and the mixture was hydrogenolyzed at atmospheric pressure and ambient temperature for 4 days. After the catalyst was filtered off, the filtrate was evaporated at reduced pressure. The residue was purified by flash column chromatography on silica eluting with chloroform/methanol (10:1), and recrystallized from isopropyl ether-hexane to give 0.27 g of 4-[N,N-bis(e-

EXAMPLE 15

Benzyl 4-[N-(2-acetoxyethyl)-N-pentylcarbamoyl]-5-(2-naphthylsulfonyl)pentanoate (Compound No. 44)

Into a solution of benzyl 4-[N-(2-acetoxyethyl)-N-pentylcarbamoyl]-5-(2-naphthylthio)pentanoate (0.50 g) in dry dichloromethane (7 ml) was added by portions of m-chloroperbenzoic acid (80%, 0.40 g) with stirring at 0° C. After stirring at room temperature for 5 hours, sodium sulfite was added to the mixture. The reaction mixture was washed with a saturated sodium bicarbonate solution and water, dried over MgSO₄, and concentrated in vacuo. The residue was purified by flash column chromatography on silica eluting with chloroform-/methanol (50:1) to give 0.47 g of benzyl 4-[N-(2-acetoxyethyl)-N-pentylcarbamoyl]-5-(2-naphthylsulfonyl)pentanoate as oil.

IR (neat): $v_{C=O}$ 1740, 1640 cm$^{-1}$
$v_{SO_2}$ 1310, 1150 cm$^{-1}$

NMR (CDCl$_3$) δ: 0.86 and 0.92(3 H, t, J=7.1 Hz), 1.1–1.7(6 H, m), 1.85–2.2(5 H, m), 2.3–2.5(2 H, m), 3.1–4.3(9 H, m), 5.0–5.15(2 H, m), 7.2–7.4(5 H, m), 7.55–7.75(2 H, m), 7.8–8.1(4 H, m), 8.48(1 H, s).

EXAMPLE 16

The compounds in the table were prepared in a similar manner to that described in example 15 (all compounds were oils).

IR (neat): $v_{C=O}$ 1730, 1650, 1640 cm$^{-1}$
$v_{SO_2}$ 1310, 1160 cm$^{-1}$

NMR (CDCl$_3$) δ: 0.8–2.5(19 H, m), 3.0–4.5(14 H, m), 7.55–7.7(2 H, m), 7.8–8.05(4 H, m), 8.50(1 H, s).

EXAMPLE 18

The compounds in the table were prepared in a similar manner to that described in example 17 (all compounds were oils).

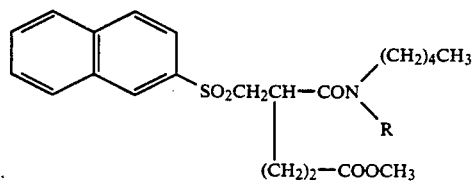

| No. | R | IR (cm$^{-1}$) | NMR (δ, CDCl$_3$) |
|---|---|---|---|
| 48 | morpholinocarbonylmethyl | 1730, 1640 (C=O) 1300, 1150 (SO$_2$) | 0.8–0.95(3H, m), 1.15–1.7(6H, m), 1.9–2.5(4H, m), 3.05–4.6(18H, m), 7.6–7.75(2H, m), 7.85–8.05(4H, m), 8.49 (1H, s) |
| 49 | 1-pyrrolidinylcarbonylmethyl | 1730, 1640 (C=O) 1310, 1150 (SO$_2$) | 0.8–2.5(17H, m), 3.1–4.4(14H, m), 7.6–7.75(2H, m), 7.85–8.05(4H, m), 8.50(1H, s) |

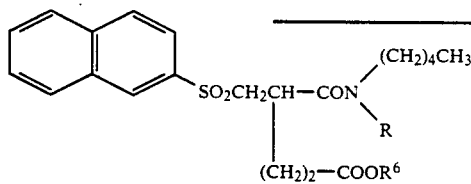

EXAMPLE 19

4-[N-(2-Acetoxyethyl)-N-pentylcarbamoyl]-5-(2-naphtylsulfonyl)pentanoic acid (Compound No. 50)

To a solution of benzyl 4-[N-(2-acetoxyethyl)-N-pentylcarbamoyl]-5-(2-naphthylsulfonyl)pentanoate (0.40

| No. | R | R$^6$ | IR (cm$^{-1}$) | NMR (δ, CDCl$_3$) |
|---|---|---|---|---|
| 45 | 2-pivaloyloxyethyl | benzyl | 1730, 1645 (C=O) 1310, 1150 (SO$_2$) | 0.86 and 0.91(3H, t, J=6.9Hz), 1.1–2.45 (19H, m), 3.1–4.3(9H, m), 5.0–5.15(2H, m), 7.25–7.4(5H, m), 7.6–7.75(2H, m), 7.8–8.05(4H, m), 8.48(1H, s) |
| 46 | 3-(2-oxo-1-pyrrolidinyl)propyl | methyl | 1730, 1680, 1635 (C=O) 1310, 1150 (SO$_2$) | 0.8–1.0(3H, m), 1.1–2.5(16H, m), 2.9–3.95(14H, m), 7.6–7.75(2H, m), 7.8–8.05 (4H, m), 8.49(1H, s) |

EXAMPLE 17

Methyl 5-(2-naphthylsulfonyl)-4-(N-pentyl-N-piperidinocarbonylmethylcarbamoyl)pentanoate (Compound No. 47)

To a solution of N-[2-(2-methoxycarbonylethyl)-3-(2-naphthylsulfonyl)propionyl]-N-pentylglycine (0.30 g), piperidine (0.12 ml) in N,N-dimethylformamide (5 ml) was added diethyl cyanophosphonate (0.1 ml) with stirring at 0° C. After stirring at room temperature for 16 hours, a dilute hydrochloric acid was added, and the reaction mixture was extracted with ethyl acetate. The organic layer was washed with a saturated sodium bicarbonate solution and water, dried over MgSO$_4$, and evaporated at reduced pressure. The residue was purified by flash column chromatography on silica eluting with chloroform/methanol (20:1) to give 0.18 g of methyl 5-(2-naphthylsulfonyl)-4-(N-pentyl-N-piperidinocarbonylmethylcarbamoyl)pentanoate as oil.

g) in acetic acid (5 ml) was added 10% Pd-C (0.05 g), and the mixture was hydrogenolyzed at atmospheric pressure and ambient temperature for 48 hours. After the catalyst was filtered off, the filtrate was concentrated in vacuo. The residue was purified by flash column chromatography on silica eluting with chloroform-/methanol (10:1) to give 0.16 g of 4-[N-(2-acetoxyethyl)-N-pentylcarbamoyl]-5-(2-naphthylsulfonyl)pentanoic acid as oil.

IR (neat): $v_{C=O}$ 1740, 1640 cm$^{-1}$
$v_{SO_2}$ 1310, 1150 cm$^{-1}$

NMR (CDCl$_3$) δ: 0.8–0.95(3 H, m), 1.1–1.7(6 H, m), 1.85–2.15(5 H, m), 2.3–2.5(2 H, m), 3.1–4.3(9 H, m), 7.55–7.7(2 H, m), 7.8–8.1(4 H, m), 8.48(1 H, s).

EXAMPLE 20

5-(2-Naphthylsulfonyl)-4-(N-pentyl-N-piperidinocarbonylmethylcarbamoyl)pentanoic acid (Compound No. 51)

To a solution of methyl 5-(2-naphthylsulfonyl)-4-(N-pentyl-N-piperidinocarbonylmethylcarbamoyl)pentanoate (0.18 g) in methanol (3 ml) was added a 1N sodium hydroxide solution (0.32 ml). After stirring at room temperature for 16 hours, the reaction mixture was concentrated in vacuo, acidified with a dilute hydrochloric acid, and extracted with ethyl acetate. The organic layer was washed with water, dried over $MgSO_4$, and evaporated at reduced pressure. The residue was recrystallized from isopropyl ether to give 0.08 g of 5-(2-naphthylsulfonyl)-4-(N-pentyl-N-piperidinocarbonylmethylcarbamoyl)pentanoic acid.

Melting point: 111°–112° C.

| | Elemental Analysis (for $C_{28}H_{38}N_2O_6S$): | | |
|---|---|---|---|
| | C % | H % | N % |
| Calcd. | 63.37 | 7.22 | 5.28 |
| Found | 63.06 | 7.31 | 5.06 |
| IR (KBr): | $\nu_{C=O}$ 1710, 1650, 1630 $cm^{-1}$ | | |
| | $\nu_{SO_2}$ 1300, 1155 $cm^{-1}$ | | |

NMR (CDCl$_3$) δ: 0.8–0.95(3 H, m), 1.05–2.55(16 H, m), 3.0–3.8(10 H, m), 4.12 and 4.60(1 H, d, J=15.9 Hz), 7.6–7.75(2 H, m), 7.8–8.05(4 H, m), 8.50(1 H, s).

EXAMPLE 21

The compounds in the table were prepared in a similar manner to that described in example 19 or 20.

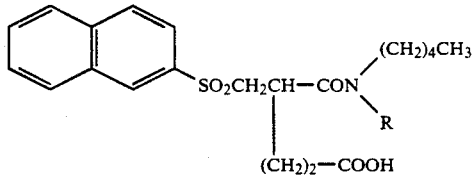

EXAMPLE 22

L-Arginine (−)-4-[N-(3-methoxypropyl)-N-pentylcarbamoyl]-5-(2-naphthylsulfonyl)pentanoic acid monohydrate In a solution of ethanol (19.5 ml) and water (1.2 ml) was dissolved (−)-4-[N-(3-methoxypropyl)-N-pentylcarbamoyl]-5-(2-naphthylsulfonyl)pentanoic acid (7.80 g) and L-arginine (2.84 g) with stirring at 40° C. Insoluble materials (e.g. trash) were collected by filtration and washed with a mixture of ethanol (7 ml) and water (1.3 ml). After combining the filtrate and washing, the mixture was allowed to stand at room temperature, and the precipitated crystals were collected by filtration to obtain 9.80 g of L-arginine (−)-4-[N-(3-methoxypropyl)-N-pentylcarbamoyl]-5-(2-naphthylsulfonyl)pentanoic acid monohydrate.

Melting point: 123°–126° C.

| | Elemental Analysis (for $C_{31}H_{51}N_5O_9S$) | | |
|---|---|---|---|
| | C % | H % | N % |
| Calcd. | 55.59 | 7.67 | 10.46 |
| Found | 55.43 | 7.63 | 10.45 |

Specific rotation: $[\alpha]_D$ −3.8° (C=1.00, $H_2O$).

EXAMPLE 23

Sodium (−)-4-[N-(3-methoxypropyl)-N-pentylcarbamoyl]-5-(2-naphthylsulfonyl)pentanoate Into a solution of (−)-4-[N-(3-methoxypropyl)-N-pentylcarbamoyl]-5-(2-naphthylsulfonyl)pentanoic acid (4.00 g) in ethanol (40 ml) was added dropwise a 1N sodium hydroxide solution (8.39 ml) with stirring at 0° C. The reaction mixture was concentrated in vacuo at 35° C., and water-ethanol (1:1, 40 ml) was added and concentrated again in vacuo to the residue. The residue was recrystallized from isopropyl ether (40 ml) to give 3.90 g of sodium (−)-4-[N-(3-methoxypropyl)-N-pentylcarbamoyl]-5-(2-naphthylsulfonyl)pentanoate as a hygroscopic amorphous solid.

TEST EXAMPLE 1

CCK-receptor binding assay in pancreas

Pancreatic plasma membranes were prepared by the method of Chang et al. (Molecular Pharmacology, Vol. 30, p. 212–, 1986). Male Wistar rats were sacrificed by

| No. | R | mp (°C.) (recryst. solvent) | IR ($cm^{-1}$) | NMR (δ, CDCl$_3$) |
|---|---|---|---|---|
| 52 | 2-pivaloyloxyethyl | amorphous | 1725, 1635 (C=O) 1305, 1150 (SO$_2$) | 0.8–0.95(3H, m), 1.05–2.15(17H, m), 2.39(2H, t, J=7.1Hz), 3.1–4.3(9H, m), 7.6–7.75(2H, m), 7.8–8.05(4H, m), 8.48(1H, s) |
| 53 | 3-(2-oxo-1-pyrrolidinyl)-propyl | amorphous | 1720, 1635 (C=O) 1150 (SO$_2$) | 0.8–0.95(3H, m), 1.1–3.95(27H, m), 7.55–7.75(2H, m), 7.8–8.05(4H, m), 8.49(1H, s) |
| 54 | morpholinocarbonylmethyl | 132–134 (isopropyl ether) | 1710, 1650, 1625 (C=O) 1305, 1155 (SO$_2$) | 0.8–1.0(3H, m), 1.1–2.55(10H, m), 3.05–4.2(14H, m), 4.44 and 4.59(1H, d, J=15.9Hz), 7.6–7.75(2H, m), 7.8–8.05 (4H, m), 8.49(1H, s) |
| 55 | 1-pyrrolidinylcarbonyl-methyl | amorphous | 1725, 1635 (C=O) 1310, 1150 (SO$_2$) | 0.8–0.95(3H, m), 1.1–2.5(14H, m), 3.1–4.15(10H, m), 4.45 and 4.53(1H, d, J=16.5Hz), 7.55–7.75(2H, m), 7.8–8.05 (4H, m), 8.49(1H, s) | decapitation and the pancreas was removed. The pancreas was dissected free from adipose tissue and minced in 50 volumes ice-cold Tris-HCl buffer (50 mM, pH 7.4 at 37° C.). Homogenization was performed using ultra disperser and the homogenate was centrifuged at 50,000×g for 10 minutes. The pellet was washed by resuspension in the same volume of fresh Tris-HCl buffer and again centrifuged as above. The final pellet was suspended in assay buffer (50 mM Tris-HCl, 5 mM MgCl$_2$, 5 mM dithiothreitol, 2 mg/ml of bovine serum albumin, and 0.14 mg/ml of bacitracin), and used as receptor sources for binding assay.

Thirty pM $^{125}$I-CCK-8 (final concentration), test drug or vehicle (for total binding) or $10^{-6}$ M CCK-8 (for nonspecific binding) were added to the assay medium containing pancreatic plasma membranes (0.5 mg of original wet weight/ml). After incubation at 37° C. for 30 minutes, the assay medium was filtrated under reduced pressure through glass fiber filter and washed four times with 4 ml of ice-cold Tris-HCl buffer. The radioactivity trapped on the filter was counted by γ-counter (Packard 5650).

Specific binding was defined as the radioactivity bound after subtracting nonspecific binding determined in the presense of $10^{-6}$M unlabeled CCK-8. IC$_{50}$ value was calculated from inhibition percentage of specific binding by each test drug.

TABLE 1

| Compound No. | IC$_{50}$ (μM) |
| --- | --- |
| 3 | 2.4 |
| 6 | 1.7 |
| 7 | 1.7 |
| 15 | 7.3 |
| 18 | 0.34 |
| 19 | 0.32 |
| 20 | 0.029 |
| 21 | 0.40 |
| 22 | 0.12 |
| 23 | 3.3 |
| 24 | 0.044 |
| 25 | 0.049 |
| 26 | 0.025 |
| 27 | 2.2 |
| 28 | 0.21 |
| 29 | 2.3 |
| 30 | 4.1 |
| 31 | 2.0 |
| 32 | 0.29 |
| 33 | 3.4 |
| 34 | 1.7 |
| 35 | 4.0 |
| 36 | 6.5 |
| 37 | 3.1 |
| 38 | 0.11 |
| 39 | 1.8 |
| 40 | 2.1 |
| 41 | 1.4 |
| 50 | 0.2 |
| 51 | 0.4 |
| 52 | 0.19 |
| 53 | 0.22 |
| 54 | 0.61 |
| 55 | 0.9 |

TEST EXAMPLE 2

CCK-antagonism in isolated gallbladder

Gallbladder strips isolated from male Hartley guinea-pig were prepared and suspended in Magnus bath filled with Krebs solution (1 g of initial tension). The solution kept at 37° C. was aerated with a mixture of 95% O$_2$ and 5% CO$_2$. The isometric contraction of strips was recorded through a force-displacement transducer. Antagonism by test drugs against gallbladder contraction induced by $10^{-8}$ M CCK-8 was examined and IC$_{50}$ value was calculated.

TABLE 2

| Compound No. | IC$_{50}$ (μM) |
| --- | --- |
| 18 | 6.8 |
| 19 | 2.1 |
| 20 | 2.6 |
| 21 | 2.9 |
| 22 | 2.8 |

TEST EXAMPLE 3

Effect on amylase secretion in rats

Male Wistar rats were anesthetized with urethane (1.5 g/kg, S.C.), and tracheal cannula was inserted. Biliopancreatic juice was collected from the cannula which had been inserted into the common bile duct. Thirty minutes after intraduodenal administration of test drug, amylase secretion was stimulated by subcutaneous injection of CCK-8 (10 μg/kg). Amylase concentration in the sample collected every 30 minutes during experiment was assayed using Amylase B Test (Wako), and ED$_{50}$ value was calculated.

TABLE 3

| Compound No. | ED$_{50}$ (mg/kg) |
| --- | --- |
| 18 | 15.7 |
| 19 | 33.3 |
| 20 | 9.6 |
| 25 | 8.0 |

What is claimed is:

1. A compound represented by the formula:

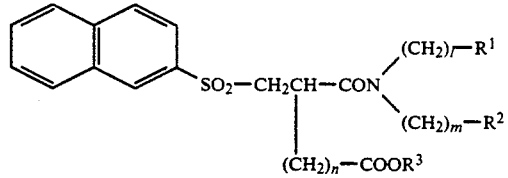

wherein R$^1$ represents a hydrogen atom, an alkyl group having 1 to 6 carbon atoms, a cycloalkyl group having 3 to 6 carbon atoms, an alkoxy group having 1 to 6 carbon atoms, an alkenyloxy group having 3 to 6 carbon atoms, an acyloxy group having 2 to 5 carbon atoms, a carboxy group, an alkoxycarbonyl group having 2 to 7 carbon atoms, a carbamoyl group of the formula

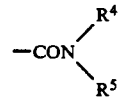

in which R$^4$ and R$^5$ are the same or different and are a hydrogen atom or an alkyl group having 1 to 6 carbon atoms, a group of the formula

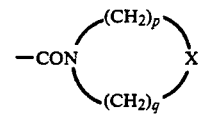

in which X is a single bond, —CH$_2$— or —O—, p and q are the same or different and are an integer of from 0 to 3, with the proviso that the sum of p and q is 2 to 5, or a lactam group of the formula

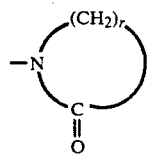

in which r is an integer of from 2 to 5; R$^2$ represents a hydrogen atom, an alkyl group having 1 to 6 carbon atoms, a cycloalkyl group having 3 to 6 carbon atoms, an alkoxy group having 1 to 6 carbon atoms, an alkenyloxy group having 3 to 6 carbon atoms, an acyloxy group having 2 to 5 carbon atoms or an alkoxycarbonyl group having 2 to 7 carbon atoms; R$^3$ represents a hydrogen atom, an alkyl group having 1 to 4 carbon atoms or a benzyl group; l and m are the same or different and are an integer of from 1 to 4; n is 1 or 2; and pharmaceutically acceptable salts thereof.

2. A compound in accordance with claim 1 wherein n has a value of 2.

3. A compound in accordance with claim 1 wherein R$^2$ is an alkyl group having 1 to 6 carbon atoms.

4. A compound in accordance with claim 1 wherein R$^1$ is an alkoxy group having 1 to 6 carbon atoms.

5. A compound in accordance with claim 1 wherein R$^3$ is a hydrogen atom.

6. A compound represented by the formula:

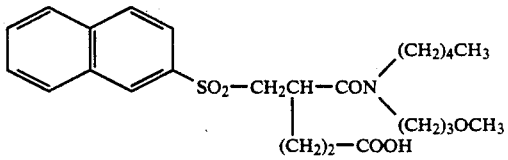

and pharmaceutically acceptable salts thereof.

7. A pharmaceutical composition containing a carrier and an effective amount of naphthylsulfonylalkanoic acid compound active ingredient or a pharmaceutically acceptable salt thereof as represented in claim 1 for the prevention and treatment of irritable bowel syndrome, biliary dyskinesia and acute pancreatitis in humans.

* * * * *